(12) United States Patent
Hogt et al.

(10) Patent No.: US 8,663,992 B2
(45) Date of Patent: Mar. 4, 2014

(54) PROCESS FOR TREATING POLYMERS CONTAINING RESIDUAL CATALYST

(75) Inventors: Andreas Herman Hogt, Enschede (NL); Wilhelm Klaas Frijlink, Zwolle (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 13/002,590

(22) PCT Filed: Jul. 8, 2009

(86) PCT No.: PCT/EP2009/058642
§ 371 (c)(1),
(2), (4) Date: Jan. 4, 2011

(87) PCT Pub. No.: WO2010/003972
PCT Pub. Date: Jan. 14, 2010

(65) Prior Publication Data
US 2011/0104812 A1    May 5, 2011

Related U.S. Application Data (60) Provisional application No. 61/153,842, filed on Feb. 19, 2009.

(30) Foreign Application Priority Data

Jul. 11, 2008    (EP) ..................... 08160202

(51) Int. Cl.
*G01N 33/20* (2006.01)
*C08G 63/08* (2006.01)
*C08G 63/06* (2006.01)

(52) U.S. Cl.
USPC ............... 436/73; 436/77; 528/354; 528/361

(58) Field of Classification Search
USPC ................ 436/73, 77; 528/354, 361
See application file for complete search history.

(56) References Cited

U.S. PATENT DOCUMENTS

| | | |
|---|---|---|
| 4,923,918 A | 5/1990 | Komori et al. |
| 2005/0192377 A1 | 9/2005 | Scheer et al. |

FOREIGN PATENT DOCUMENTS

| | | |
|---|---|---|
| JP | 2001 026658 | 1/2001 |
| WO | WO 95 18169 | 7/1995 |
| WO | WO 2009 121830 | 10/2009 |

OTHER PUBLICATIONS

A Sodergard and J.H Nasman: "Melt Stability Study of Various Types of Poly(L-Lactide)" Ind. Eng. Chem Res., vol. 35, No. 3, 7 Mar. 1996, pp. 732-735.

Lawrence L. Stookey: Analytic Chemistry, vol. 42, No. 7, Jun. 1970, pp. 779-781.

(Continued)

*Primary Examiner* — Krishnan S Menon
*Assistant Examiner* — Dwan A Gerido
(74) *Attorney, Agent, or Firm* — Timothy D. Meade (57) ABSTRACT

Process for thermally stabilizing a polymer containing residues of a Sn(II), Sb(III), Pb(II), Bi(III), Fe(II), Ti(II), Ti(III), Mn(II), Mn(III), or Ge(II)-containing catalyst by treating the polymer at a temperature above its melting temperature with a peroxide selected from the group consisting of ketone peroxides, hydroperoxides, peracids, hydrogen peroxide, and mixtures thereof, wherein said peroxide is used in an amount less than 0.2 wt % based on the weight of the polymer and wherein the molar ratio of peroxy functionalities from said peroxide (p) to metal (M) ranges from 1 to 100; said metal (M) being selected from the group consisting of Sn(II), Sb(III), Pb(II), Bi(III), Fe(II), Ti(II), Ti(III), Mn(II), Mn(III), and Ge(II). The invention further relates to a method for determining the metal residue content of a polymer.

16 Claims, 3 Drawing Sheets

(56) References Cited

OTHER PUBLICATIONS

Tsutomu Shimotori et al., "A Polymer Membrane Containing Fe° as a Contaminant Barrier", Environmental Science & Technology, vol. 38, No. 7, 2004, pp. 2264-2270.

Stanley J. Bajic and Bruno Jaselskis, "Indirect Spectrophotometric Determination of Micro-amounts of Tin (II) in the Presence of Tin (IV) and in Dental Gels", Analyst, Oct. 1991, vol. 116, pp. 1059-1061.

Bruno H. Zimm and Walter H. Stoclanayer, "The Dimensions of Chain Molecules Containing Branches and Rings", Journal of Chemical Physics, Dec. 1949, vol. 17, No. 12, pp. 1301-1314.

A.P. Gupta and Vimal Kumar, "New emerging trends in synthetic biodegradable polymers—Polylactide: A critique", European Polymer Journal, vol. 43 (2007), pp. 4053-4074.

M. Hartmann, "High Molecular Weight Polylactic Acid Polymers" in Biopolymer Renewable Resources, Chapter 15, 1998, pp. 367-411.

International Search Report and Written Opinion, PCTEP2009/058642, mailed Feb. 8, 2010.

Reply to Written Opinion, PCT/EP2009/058642, dated Apr. 23, 2010.

International Preliminary Report on Patentability, PCT/EP2009/058642, mailed Oct. 19, 2010.

ACD 10028 P1-JP Office Action English language translation for Patent Application No. 2011-517151 dated Jun. 26, 2012.

PROCESS FOR TREATING POLYMERS CONTAINING RESIDUAL CATALYST

REFERENCE TO RELATED APPLICATION(s)

This application is the U.S. National Phase of PCT/EP2009/058642 filed on Jul. 8, 2009 and claims the benefit of U.S. Provisional Application No. 61/153,842 filed on Feb. 19, 2009.

Biodegradable polymers constitute a group of materials subject to continued development. Among them are poly (hydroxy acids), which are polymers made from monomers containing both a carboxylic acid group and a hydroxyl group. Examples of such polymers include polylactic acid (i.e. polylactide, PLA), poly(hydroxybutyrate), polyglycolide, and poly($\epsilon$-caprolactone). Polylactic acid, which is most often prepared from lactide (i.e. lactic acid dimer) is presently used for medical applications like sutures, degradable bone nails, and controlled release of drugs.

At present, there is increased interest in the use of polylactic acid for other than medical applications, such as hygiene products, agricultural films, and packaging applications, just to name a few.

Polylactic acid can be produced directly by polycondensation reactions that are typical in polyesters production. The highest molar masses are however achieved by ring opening polymerization of lactide. This ring opening polymerization requires the use of a catalyst. Sn(II)-containing catalysts, in particular Sn(II) 2-ethylhexanoate (commonly referred to as tin(II) octoate) is the most widely used catalyst for this purpose, but also Sb, Pb, and Bi-containing catalysts are known as suitable catalysts.

One major disadvantage of PLA is its poor thermal and hydrolytic stability, which causes problems in the processing control and gives undesirable properties of the final product. The melt degradation of PLA has been widely studied, and one of the main reasons for the undesired degradation seems to be depolymerization catalysed by residues of the catalyst. It has been found that addition of certain peroxides can deactivate residual tin catalyst in the polymer, thereby retarding the melt degradation (Södergaård and Näsman, *Ind. Eng. Chem. Res.*, vol. 35, 1996, pp. 732-735).

This document, however, does not disclose the amounts of peroxide, based on polymer weight, and the peroxide/Sn(II) ratio required and used.

Hence, there is a need for optimising the process for thermally stabilizing PLA. This optimisation is the object of the present invention.

The inventors have found that the thermal stability of PLA can be optimised by tuning the peroxide concentration and the peroxide/Sn(II) molar ratio. More in particular, it has been found that improved thermal stability, i.e. minimised degradation, can be obtained by using specific types of peroxides and in a limited concentration range, relative to resin and Sn(II). The same effect occurs with Sb(III), Pb(II), Bi(III), Fe(II), Ti(II), Ti(III), Mn(II), Mn(III), and Ge(II)-containing catalysts.

Sn(II), Sb(III), Pb(II), Bi(III), Fe(II), Ti(II), Ti(III), Mn(II), Mn(III), or Ge(II)-containing catalysts are also used in the preparation of other polymers, in particular those which also involve ring-opening polymerization. The same positive effects of the type and amount of peroxide can be obtained by applying the process of the present invention to such other polymers.

Although the use of peroxide is required in the present process for deactivating residual Sn(II), Sb(III), Pb(II), Bi(III), Fe(II), Ti(II), Ti(III), Mn(II), Mn(III), and Ge(II), the amount of peroxide used should be relatively low in order to minimise changes to the polymer chains and to reduce the amount of peroxide decomposition products in the final product. Such decomposition products may cause yellow discoloration, may leave odour and/or taste, and their presence is thus undesired for products which are intended for food contact. Especially the decomposition products of aromatic peroxides, such as cumyl hydroperoxide, are known to give these unwanted side-effects.

The present invention therefore relates to a process for thermally stabilizing a polymer containing residues of a Sn(II), Sb(III), Pb(II), Bi(III), Fe(II), Ti(II), Ti(III), Mn(II), Mn(III), or Ge(II)-containing catalyst by treating the polymer at a temperature above its melting temperature with a peroxide selected from the group consisting of ketone peroxides, organic hydroperoxides, peracids, hydrogen peroxide, and mixtures thereof, wherein said peroxide is used in an amount less than 0.2 wt % based on the weight of the polymer and wherein the molar ratio of peroxy functionalities from said peroxide (p) to metal (M)—i.e. p/M—ranges from 1 to 100; M being selected from groups consisting of Sn(II), Sb(III), Pb(II), Bi(III), Fe(II), Ti(II), Ti(III), Mn(II), Mn(III), and Ge(II). Most preferably, M is Sn(II). A procedure for determining the metal (M) content of the polymer is described below.

The molar ratio p/M should be below 100, preferably from 1 to 50, more preferably from 1 to 20, and most preferably from 1 to 10, in order to minimize degradation of the polymer. The molar ratio p/M should be at least 1 in order to have effective deactivation of the residual metal-containing catalyst, improved colour (reduced yellowing) and improved transparency of the polymer.

The number of peroxy functionalities (p) is defined as the total number of —O—O-functionalities present in and originating from the peroxide selected from the group consisting of ketone peroxides, organic hydroperoxides, peracids, hydrogen peroxide, and mixtures thereof. Hence, 1 mol of peroxy functionalities refers to the number of moles of said peroxide times the number of peroxy functionalities per molecule of said peroxide. The number of peroxy functionalities does not include any peroxy functionalities originating from other types of peroxides than ketone peroxides, organic hydroperoxides, peracids, hydrogen peroxide, and mixtures thereof.

The amount of the peroxide selected from the group consisting of ketone peroxides, organic hydroperoxides, peracids, hydrogen peroxide, and mixtures thereof, used in the process should be less than 0.2 wt %, preferably less than 0.15 wt %, more preferably less than 0.1 wt %, based on the weight of the polymer. The amount of said peroxide used in the process is preferably higher than 0.0001 wt %, more preferably higher than 0.0002 wt %, and most preferably higher than 0.0005 wt %, based on the weight of the polymer.

In addition to ketone peroxides, organic hydroperoxides, peracids, hydrogen peroxide, and mixtures thereof, other peroxides may be present during the process, if so desired. However, in calculating the amount of peroxide of less than 0.2 wt % and the molar ratio of peroxy functionalities to M, this additional other peroxide should not be taken into account.

The peroxide to be used in the process of the present invention is selected from the group consisting of ketone peroxides, organic hydroperoxides, peracids, hydrogen peroxide, and mixtures thereof. The peroxide preferably has a low water content and is not admixed with solvents, especially those that may cause hydrolysis and/or transesterification of the polymer, such as phthalates. More preferably, the peroxide is used in its pure form.

Organic peroxides, and more particularly ketone peroxides, hydroperoxides, and mixtures thereof are the preferred peroxides. Most preferably, the peroxide is a hydroperoxide.

Examples of suitable ketone peroxides are methyl isobutyl ketone peroxide, methyl ethyl ketone peroxide, methyl isopropyl ketone peroxide, acetyl acetone peroxide, and cyclohexanone peroxide.

Examples of suitable hydroperoxides include cumyl hydroperoxide, 1,1,3,3-tetramethylbutyl hydroperoxide, t-butyl hydroperoxide, 1,2-diisopropylbenzene monohydroperoxide, t-amyl hydroperoxide, t-hexyl hydroperoxide, hexyleneglycol hydroperoxide, 1,2,3,4-tetrahydro-1-naphthyl hydroperoxide, m/p-diisopropylbenzene hydroperoxide, ethylbenzene hydroperoxide, 1,4-diisopropylbenzene dihydroperoxide, 1,3-diisopropylbenzene dihydroperoxide, p-menthane hydroperoxide, 2,5-dihydroperoxy-2,5-dimethylhexane, pinane hydroperoxide, and 2-isopropyl naphthyl hydroperoxide.

The preferred peroxide for use in the process of the present invention is 1,1,3,3-tetramethylbutyl hydroperoxide, as it is a non-aromatic peroxide that can be prepared safely in pure form with low water content and gives the best thermal stability of the polymer.

Polymers that can be thermally stabilized by the process of the present invention include any polymer that contains residues of a Sn(II), Sb(III), Pb(II), Bi(III), Fe(II), Ti(II), Ti(III), Mn(II), Mn(III), or Ge(II)-containing catalyst. This particularly applies to polymers prepared by ring-opening melt polymerization. More preferably, the process is used to treat poly(hydroxy acids), such as PLA, poly(hydroxybutyrate), polyglycolide, poly(ε-caprolactone), and copolymers and blends thereof. Even more preferably, the process of the present invention is used to treat polylactic acid, including poly(L-lactide) (PLLA) and poly(D-lactide) (PDLA).

The polymer to be treated by the process of the present invention preferably has a weight average molecular weight ($M_w$) of 20,000-500,000, more preferably 40,000 to 400,000. The number average molecular weight is preferably ($M_n$) 10,000 to 300,000, more preferably 10,000 to 200,000.

The Sn(II), Sb(III), Pb(II), Bi(III), Fe(II), Ti(II), Ti(III), Mn(II), Mn(III), or Ge(II)-content of the polymer will generally be in the range 1 to 1,000 ppm, more particularly 10 to 500 ppm.

This metal content can be determined according to the following procedure: (i) dissolving the polymer in an organic solvent, said solvent being able to phase separate with water, (ii) adding an aqueous Fe(III) solution, (iii) shaking the resulting 2-phase system thereby oxidizing the metal and reducing Fe(III) to Fe(II), (iv) adding water, (v) complexing the resulting Fe(II) in the water layer with a complexing agent resulting in a coloured Fe(II)-complex, (vi) determining the Fe(II) content using spectrophotometry, and (vii) deducing from said Fe(II) content the metal content of the polymer.

In a preferred embodiment, Fe(III) is added to the dissolved polymer as an acidic solution, more preferably a HCl-containing solution.

Examples of suitable complexing agents for Fe(II) are 3-(2-pyridyl)-5,6-diphenyl-1,2,4-triazine-4,4'-disulphonic acid monosodium salt (also known as FerroZine®), 3-(2-pyridyl)-5,6-di(2-furyl)-1,2,4-triazine-5',5"-disulphonic acid disodium salt (also known as Ferene), 2,4,6-tripyridyl-(2)-1,3,5-triazine (TPTZ), 4,7-diphenyl-1,10-phenanthroline (also known as bathophenanthroline), 1,10-phenanthroline (also known as ortho-phenanthroline), and 4,7-dihydroxy-1,10-phenanthroline. A preferred complexing agent for Fe(II) is 3-(2-pyridyl)-5,6-diphenyl-1,2,4-triazine-4,4'-disulphonic acid monosodium salt (FerroZine®) in a pH 4.8 buffered aqueous medium. The absorbance of the resulting pink colored solution can be measured spectrophotometrically at $\lambda$=562 nm.

Examples of suitable organic solvents are dichloromethane, chloroform, and toluene. The organic solvent should be able to dissolve the polymer and to phase separate with water, thereby allowing the redox reaction of the residual metal and Fe(III) to take place at the water-organic interface.

The above method allows for the determination of very small amounts of the above-mentioned low oxidation state metals (e.g. Sn(II)), even in the presence of their higher oxidation state counterparts (e.g. Sn(IV). The invention therefore also relates to a method for analyzing residues of Sn(II), Sb(III), Pb(II), Bi(III), Fe(II), Ti(II), Ti(III), Mn(II), Mn(III), or Ge(II)-containing catalyst in a polymer according to the above steps. In contrast to the method described by S. J. Bajic and B. Jaselskis (*Analyst*, vol. 116 (1999) 1059-1061), the method according to the present invention uses an organic solvent in addition to water, whereas the prior art method uses completely aqueous systems. As a result—and in contrast to the prior art method—the method according to the present invention allows for the determination of metals that are present in water-insoluble polymers. It further allows for the determination of metals that are present as water insoluble complexes.

The catalyst preferably is a Sn(II)-containing catalyst, more preferably an organo-tin(II) compound, most preferably tin(II) 2-ethylhexanoate.

The thermal stabilization of the polymer according to the process of the present invention is performed by treating the polymer with the peroxide at a temperature above the melting temperature of the polymer. The term "melting temperature" refers to either the melting point or melting range of the polymer, whichever is applicable.

For most polymers, this melting temperature will be above 60° C. (polycaprolactone), more preferably above 130° C., and most preferably above 150° C. It will be understood that the temperature should be below the degradation temperature of the polymer. Hence, the temperature is preferably below 300° C., more preferably below 275° C., and most preferably below 250° C. For PLA, the temperature is preferably in the range 150 to 250° C., more preferably 160 to 240° C., and most preferably 170 to 230° C.

The peroxide is preferably added to the melted polymer towards the end of the polymerization process, before extrusion and pelletisation. Alternatively, the peroxide can be added to the polymerization reactor after polymerization has been completed, or can be dosed to the polymer melt during extrusion.

During processing, various additives can be added to the polymer in order to tailor the polymer to its intended end-use. Examples of such additives are plasticizers, pigments, antioxidants, fillers and other processing aids. Suitable plasticizers are generally available commercial plasticizers like di- or tricarboxylic acid esters, epoxide oils or esters, polymeric polyesters, aliphatic diesters, alkylether mono- or diesters, glycerine esters, and blends thereof. A suitable amount of plasticizer is 0.5-30 wt %, based on the weight of polymer. Suitable fillers are the conventional inorganic or organic fillers, like calcium carbonate, kaolin, mica, talc, silicium oxide, zeolite, nano-fillers, glass fibers or spheres, starch, and saw dust. A suitable amount of filler is 0.5-50 wt % based on the weight of polymer.

EXAMPLES

Methods
Melt Flow Index

The melt-flow index (MFI) was measured with a Göttfert® Melt indexer Model MP-D according to DIN 53735/ASTM 1238 (190° C., 21.6 N load). The MFI is expressed in g/10 min.

Molecular Weight Characterization and Branching

The molecular weight of the polymers was determined using a size-exclusion chromatography (SEC)-system consisting of a Pump: Knauer Smartline pump 1000
Eluent: 1,1,1,3,3,3-Hexafluoroisopropanol (HFIP)
Flow: 0.6 ml/min
Injection: Spark Holland Triathlon autosamples, 50 µl
Concentration: about 2 mg/ml
Solvent: 1,1,1,3,3,3-Hexafluoroisopropanol
Column: 2×PSS PFG linear XL 7µ, 300×8 mm
Detection: Viscotek TDA 302 Tetra Detector Array The molecular weights of the samples, i.e. the number-average (Mn), weight-average (Mw), and z-average (Mz) molecular weights, were calculated from Light Scattering (LS) detection. The dispersity (D) was calculated as Mw/Mn. The Intrinsic Viscosity (IV) was determined in the viscometer detector. From the Mark-Houwink plots, the branching number (Bn, i.e. the average number of branches per molecule) and the frequency ($\lambda$, i.e. the branching per 100 monomeric units) were calculated according to the theory of Zimm and Stockmayer, *J. Chem. Phys.* 17 (1949) 1301. The structure factor $\epsilon$ for randomly branched polymers was taken as 0.75.

Colour

The colour of the granulated samples was compared visually.

Thermal Stability

Prior to the analysis the samples were dried overnight in a vacuum oven at 50° C., resulting in residual water contents of approx. 0.1%. The thermal stability of the extruded materials was measured at 220° C. during 30 minutes under nitrogen atmosphere using a 5 cm$^3$ micro-extruder from DSM (serial no. 97023).

Determination Sn(II)

In order to minimize Sn(II) to be oxidized by air-oxygen, all glassware and reagents were purged with nitrogen gas.

A PLA sample (0.5-1.0 g) was weighed into a 30-ml GC-vial. Dichloromethane (15 ml) was added to said vial while purging with nitrogen gas. The vial was capped and all subsequent additions were done through the septum. FeCl$_3$ solution (0.5 ml, 0.1 M) was added and the vial was shaken for 30 minutes. Water (5 ml) was added and the vial was shaken for another 10 minutes. Another 10 ml water was then added, resulting in the positioning of some PLA precipitate at the interface of the two layers. The water layer was transferred to 50-ml volumetric flask and was further diluted with water to approximately 35 ml. 10 ml buffer solution and 3 ml FerroZine® solution were added and the total volume was set at 50 ml with water.

The absorbance of the resulting pink colored solution versus water in a 1-cm cell at 562 nm was measured using a spectrophotometer (Dr. Lange LICO 200 Spectrophotometer).

The FeCl$_3$ solution was prepared by dissolving 48 g of ammonium iron(III) sulphate.12 aq in 500 ml water and 200 ml of 36% HCl, and diluting to 1 litre with water.

The buffer solution was prepared by adding 100 ml glacial acetic acid to 500 ml water, adjusting the pH to 4.8 using a 50% m/m NaOH solution, and diluting the solution to 1 litre with water.

The FerroZine® solution was a 0.02 M solution of 3-(2-pyridyl)-5,6-diphenyl-1,2,4-triazine-4,4'-disulphonic acid monosodium salt in water.

Comparative Example 1

Polylactic acid (PLA) granules (ex NatureWorks) were added to a W&P ZSK30 extruder (L/D=36) using a Sympatec vibrating conveyer placed on a KTRON 1 balance for measuring throughput. The screw speed of the extruder was 200 rpm; the screw length 1,150 mm.

The following temperature profile was used in the extruder: 220-220-220-220-220-220° C. Nitrogen atmosphere was applied at hopper and die.

1,1,3,3-Tetramethylbutyl hydroperoxide (TMBH Special, ex AkzoNobel) was injected to the polylactic acid melt at a screw length of 439 mm. Vacuum degassing was started at a screw length of 895 mm. Injection of peroxide was performed using a Knauer (supplied by Separations) 10 ml dosing pump with pressure readout and high-pressure restriction. The dosing head was cooled with water.

The amounts of TMBH added were (based on polylactic acid): 0.25 wt % and 0.5 wt %.

The extruded strands were fed through a cooling water bath and granulated using an Automatik ASG5 granulator. The granulated PLA samples were dried overnight in a circulation oven at 50° C.

The MFI, the molecular weight distribution, the branching number and frequency of the resulting modified polylactic acid were determined according to the procedures explained above. The results are presented in Table 1.

TABLE 1

| Peroxide | MFI | $M_n$ | $M_w$ | $M_z$ | D | IV | Lambda | Bn |
|---|---|---|---|---|---|---|---|---|
| none | 13.8 | 50,000 | 84,000 | 129,000 | 1.68 | 1.17 | 0.001 | 0.01 |
| 0.25 wt % TMBH | 26.6 | 35,000 | 70,000 | 114,000 | 2.00 | 1.00 | 0.004 | 0.08 |
| 0.5 wt % TMBH | 36.3 | 33,000 | 66,000 | 111,000 | 2.00 | 0.93 | 0.02 | 0.27 |

This table shows that the use of TMBH at concentrations in the range of 0.25-0.5 wt % resulted in an increased MFI, i.e. a distinct degradation of polylactic acid. Surprisingly, also long chain branching on the linear polymer chain occurred.

Example 2

Comparative Example 1 was repeated, except that a different polylactic acid grade ex Purac was used, TMBH was formulated on polylactic acid powder prior to the extrusion instead of dosing directly to the polymer melt in the extruder, and the extrusion was run at lower temperatures on a smaller Haake extruder instead of the ZSK30 extruder (both twin-screw extruders). The amounts of TMBH added were substantially lower than in Comparative Example 1 in order to minimize degradation of the polylactic acid due to the peroxide during compounding.

The polylactic acid used in this Example—Purasorb®, a biomedical Poly-L-lactide (PLLA) powder grade (ex Purac)—was the powder grade PLA available on the market with the lowest possible Sn content.

Compounds were prepared from this PLLA powder grade by adding tin(II) 2-ethylhexanoate (ex Sigma, referred to as Sn-Oct$_2$) and a metal deactivator (cat-killer). The cat-killers used in this Example are TMBH and Irganox® MD1024 (2',3-bis[[3-[3,5-di-tert-butyl-4-hydroxyphenyl]propionyl]] propiono hydrazide, ex Ciba).

In the experiments where TMBH was used as cat-killer, Sn-Oct$_2$ and TMBH were very well formulated, via solutions in dichloromethane, on separate portions of the PLLA. The dichloromethane was allowed to evaporate from the PLLA for approx. 2 hours under nitrogen purge.

Where Irganox® MD1024 was used as cat-killer, this material was added as such (powder) to the PLLA.

Subsequently, separate formulations of Sn-Oct$_2$/PLLA and metal deactivator/PLLA were combined and very well mixed.

The resulting compounds were added, using a Plasticolor 2000 feeder, to a Haake Rheocord 9000 extruder equipped with Rheomex TW100 (intensive mixing screws). The screw speed of the extruder was 200 rpm. The following temperature profile was used in the extruder (zones 1-4): 130-180-180-180° C. Nitrogen atmosphere was applied at hopper and die. The extruded strands were fed through a cooling water bath and granulated using an Automatik ASG5 granulator. The granulated PLLA samples were dried overnight in a circulation oven at 50° C.

The MFI of the resulting modified polylactic acid was determined according to the procedure explained above. The results are presented in Table 2.

TABLE 2

| Cat-killer | Sn-Oct$_2$ | Cat killer/Sn(II) molar ratio | MFI | Colour |
|---|---|---|---|---|
| none | none | — | 6.0 | very slightly yellow |
| none | 500 ppm | — | n.m. | yellow |
| 0.02 wt % TMBH | 500 ppm | 1 | 7.5 | slightly yellow |
| 0.04 wt % TMBH | 500 ppm | 2 | 7.0 | slightly yellow |
| 0.04 wt % TMBH | none | — | 6.4 | very slightly yellow |
| 0.1 wt % MD1024 | 500 ppm | 1.5 | n.m. | slightly yellow |
| 0.25 wt % MD1024 | 500 ppm | 4 | 325 | slightly grey | n.m. = not measurable (too low viscosity, MFI > 325)

The measured polymer melt temperatures in zones 1, 2 and 4 of the Haake extruder were approx. 155° C., 183° C. and 212° C.

This table shows that the use of TMBH according to the present invention very effectively suppresses the degradation of polylactic acid during compounding by deactivation of the Sn(II) catalyst, as compared to the reference cat-killer MD1024.

Figure 1:
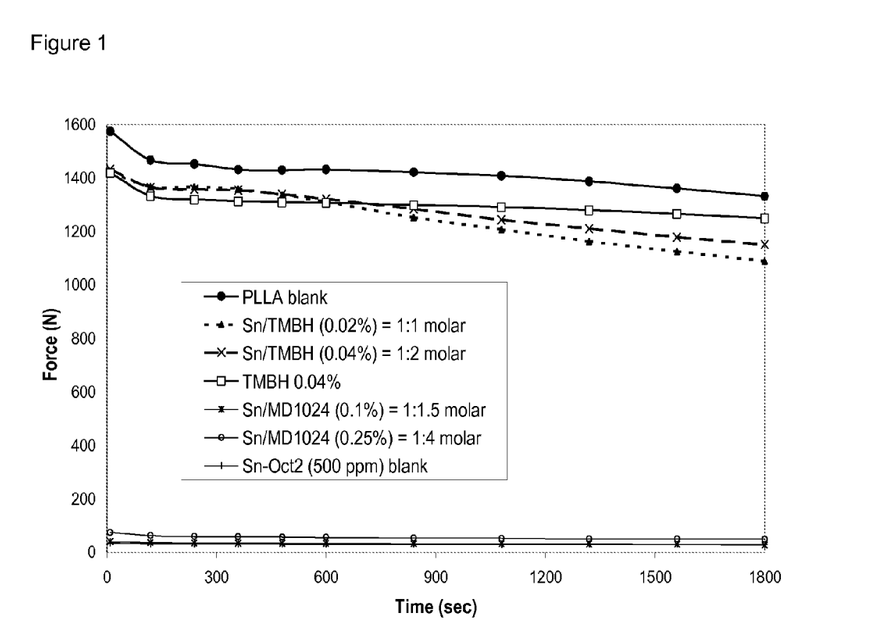
FIG. 1: PLA heat stability curves of Force vs. time at 220° C. for PLA compounds made using 500 ppm Sn-Oct$_2$ (see Table 2). Mean curves of duplicate analysis are presented.

In the subsequent thermal stability tests (see FIG. 1) no significant additional degradation of PLA treated according to the process of the present invention occurred at 220° C. in the first 10 minutes. At prolonged heating the higher TMBH concentration seemed to be favourable.

Furthermore, TMBH acts as a bleaching agent resulting in less yellow discoloration of the modified polylactic acid compared to the PLLA/500 ppm Sn-Oct$_2$ blank compound.

Example 3

Example 2 was repeated, except that 50 ppm Sn-Oct$_2$ was added (instead of 500 ppm) and the amounts of TMBH added were lowered correspondingly.

Trigonox® K-90 (cumyl hydroperoxide, 90% solution in aromatic solvent mixture, ex Akzo Nobel, referred to as CHP) and MIBKP (methyl isobutyl ketone peroxide, 40% solution in isoparaffins) were also tested as cat-killer.

In one experiment, MD1024 was added to the PLLA powder via a solution in acetone to assure homogeneous distribution in order to compare it with addition of MD1024 as powder (melting range 221-232° C.).

Compounds were prepared from PLLA powder, Sn-Oct$_2$ and a metal deactivator (cat-killer). Sn-Oct$_2$ and peroxide were very well formulated, via solutions in dichloromethane, on separate portions of the PLLA. MD1024 was either added as such (powder) or dissolved in acetone and formulated on the PLLA. The dichloromethane, respectively acetone, were allowed to evaporate from the PLLA for approx. 2 hours under nitrogen purge. Subsequently, the separate formulations of Sn-Oct$_2$/PLLA and metal deactivator/PLLA were combined and very well mixed.

The resulting compounds were extruded and granulated as described in Example 2. The granulated PLLA samples were dried overnight in a circulation oven at 50° C.

The MFI of the resulting modified polylactic acid was determined according to the procedure explained above. The results are presented in Table 3.

TABLE 3

| Cat-killer | Sn-Oct$_2$ | cat-killer/Sn(II) molar ratio | MFI |
|---|---|---|---|
| none | none | — | 5.8 |
| none | 50 ppm | — | 6.6 |
| 0.002 wt % TMBH | 50 ppm | 1$^a$ | 5.7 |
| 0.004 wt % TMBH | 50 ppm | 2$^a$ | 5.7 |
| 0.02 wt % TMBH | 50 ppm | 10$^a$ | 6.0 |
| 0.004 wt % CHP | 50 ppm | 2$^a$ | 5.9 |
| 0.004 wt % MIBKP | 50 ppm | 1.5$^a$ | 5.8 |
| 0.1 wt % MD1024 (in acetone) | 50 ppm | 15$^b$ | 8.1 |
| 0.1 wt % MD1024 (as powder) | 50 ppm | 15$^b$ | 8.1 |
| 0.25 wt % MD1024 (as powder) | 50 ppm | 40$^b$ | 7.7 |

$^a$molar ratio peroxy functionality/Sn(II)
$^b$molar ratio catkiller/Sn(II)

The measured polymer melt temperatures in zones 1, 2 and 4 of the Haake extruder were approx. 158° C., 181° C. and 191° C.

Figure 2:
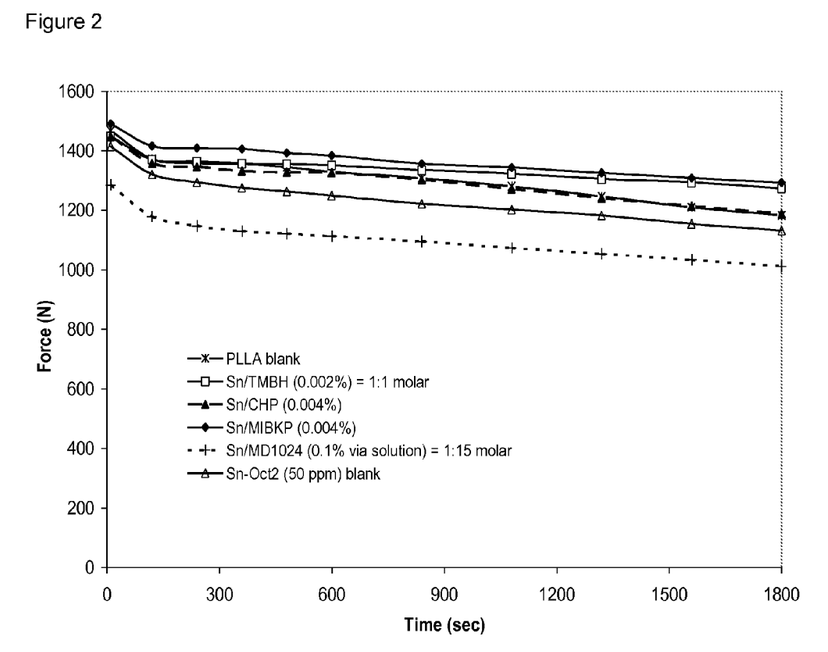
FIG. 2: PLA heat stability curves of Force vs. time at 220° C. for PLA compounds made using 50 ppm Sn-Oct$_2$ (see Table 3). Mean curves of duplicate analysis are presented.
Figure 3:
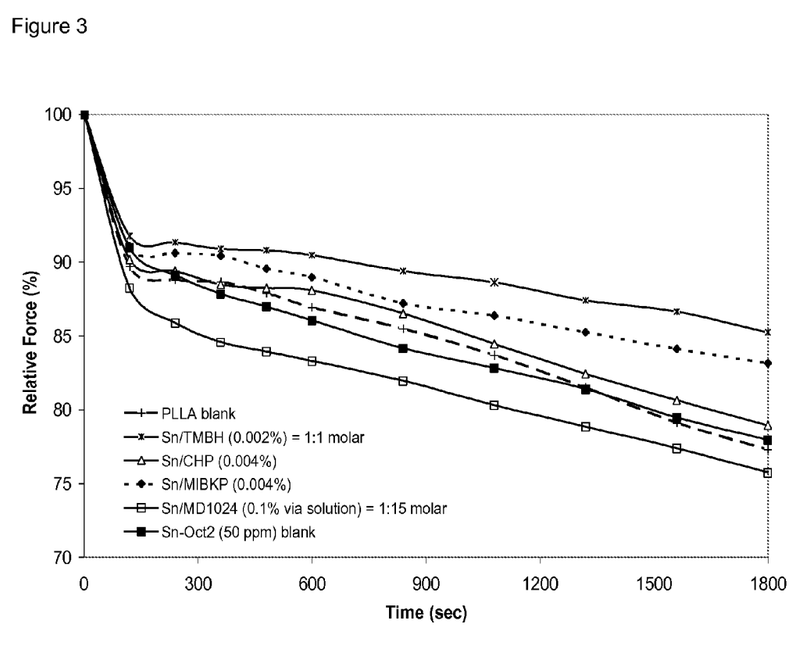
FIG. 3: PLA heat stability curves of Relative Force vs. time at 220° C. for PLA compounds made using 50 ppm Sn-Oct$_2$ (see Table 3). Mean curves of duplicate analysis are presented.

The trends in MFI observed in Example 2 can also be seen in Table 3, although the PLLA degradation due to the Sn(II) catalyst was less pronounced. It is thus confirmed that even with a molar ratio of peroxy functionalities:Sn(II) of 1:1, the use of TMBH according to the present invention effectively suppresses the degradation of polylactic acid during compounding by deactivation of the Sn(II) catalyst, as compared to the reference cat-killer MD1024. The same effect was observed using aromatic hydroperoxide (CHP) and ketone peroxide (MIBKP) instead of aliphatic hydroperoxide (TMBH). Additions of 0.1 wt % MD1024 as powder and via a solution resulted in the same MFI after compounding. However, the MFI was higher than the PLLA/50 ppm Sn-Oct$_2$ blank compound. In the subsequent thermal stability tests (FIGS. 2 and 3), no significant additional degradation of PLLA treated according to the process of the present invention occurred at 220° C. in the first 10 minutes. At prolonged heating TMBH showed the best stabilizing effect of all tested cat-killers, even better than the PLLA blank.

Furthermore, it seems favourable to overdose TMBH (vs. Sn-Oct$_2$) as it not only effectively deactivates the Sn(II) catalyst (see table 3: 0.02% TMBH), but also reduces the yellow discoloration of the modified polylactic acid (see table 2: 0.02% TMBH). However, the amount of peroxide should not be too high, because, as seen in Table 1, this will lead to degradation of the polymer.

Example 4

In order to illustrate the procedure described above for the determination of the Sn(II) content in PLA, the Sn(II) content of a sample of unstabilized PLA (granules) was determined according to the procedure described above. PLA samples (0.5 g or 1.0 g) were used and the measurements were done in 5-fold. Also a reagent blank determination was carried out in 5-fold. The results are summarized in Table 4.

TABLE 4

| Experiment | Sample weight (g) | Absorbance $\lambda$ = 562 nm | Sn(II) found ($\mu$g) | Sn(II) content (mg/kg) |
| --- | --- | --- | --- | --- |
| Reagent blank[1] | | 0.044 | | |
| | | 0.052 | | |
| | | 0.050 | | |
| | | 0.053 | | |
| | | 0.047 | | |
| PLA[2] | 0.5529 | 0.088 | 4.2 | 7.7 |
| | 0.5110 | 0.084 | 3.8 | 7.4 |
| | 0.5054 | 0.085 | 3.9 | 7.7 |
| | 0.5040 | 0.091 | 4.6 | 9.1 |
| | 0.5218 | 0.093 | 4.8 | 9.2 |
| Reagent blank | | 0.070 | | |
| | | 0.070 | | |
| PLA | 0.5335 | 0.109 | 4.2 | 7.9 |
| | 0.5150 | 0.106 | 3.9 | 7.6 |
| PLA | 0.9780 | 0.122 | 5.7 | 5.8 |
| | 0.9423 | 0.110 | 4.3 | 4.6 |

[1] mean absorbance: 0.049, s = 0.004, n = 5
[2] mean Sn(II) content: 8.2 mg/kg, s = 0.9 mg/kg, n = 5

In the next experiment, Sn(II) standard solutions were prepared by dissolving known amounts of a validated standard Sn(II) 2-ethylhexanoate in dichloromethane (oxygen-free). From these standard solutions known amounts were taken and added to the dichloromethane layer of the PLA sample, and the procedure as described above was continued. Different spiking amounts were used, respectively with 0.5 g and 1.0 g of PLA sample. The recovery results are shown in Table 5.

TABLE 5

| Experiment | Sample weight (g) | Sn(II) spiked ($\mu$g) | Absorbance $\lambda$ = 562 nm | Sn(II) found ($\mu$g) | Recovery (%) |
| --- | --- | --- | --- | --- | --- |
| PLA | 0.5054 | | 0.085 | 3.9 | |
| | 0.5218 | | 0.093 | 4.8 | |
| PLA + spike | 0.5048 | 41.6 | 0.398 | 38.8 | 84 |
| | 0.5209 | 102.7 | 0.981 | 101.2 | 94 |
| | 0.5074 | 116.6 | 1.036 | 107.3 | 89 |
| PLA | 0.5335 | | 0.109 | 4.2 | |
| | 0.5150 | | 0.106 | 3.9 | |
| PLA + spike | 0.5178 | 6.8 | 0.159 | 9.7 | 83 |
| | 0.5142 | 7.4 | 0.148 | 8.5 | 61 |
| PLA | 0.9780 | | 0.122 | 5.7 | |
| | 0.9423 | | 0.110 | 4.3 | |
| PLA + spike | 0.9824 | 9.4 | 0.175 | 11.4 | 68 |
| | 1.0064 | 18.1 | 0.271 | 21.8 | 93 |

The results in Tables 4 and 5 show that the method according to the present invention for the analysis of Sn(II) in PLA is robust and sensitive. The method can be used for the analysis of very low Sn(II) contents. Spiked Sn(II) amounts are recovered sufficiently well, even at very low addition levels. This indicates that the reaction between Sn(II) and Fe(III) at the interface of the two layers takes place efficiently, even though Sn(II) is present in the form of a complex (e.g. as Sn(II)octoate), and that interference by air-oxygen can be excluded sufficiently.

The invention claimed is:

1. A process for thermally stabilizing a polymer containing residues of a Sn(II), Sb(III), Pb(II), Bi(III), Fe(II), Ti(II), Ti(III), Mn(II), Mn(III), or Ge(II)-containing catalyst, the process comprising: treating the polymer at a temperature above its melting temperature with a peroxide selected from the group consisting of ketone peroxides, organic hydroperoxides, peracids, hydrogen peroxide, and mixtures thereof, wherein said peroxide is used in an amount less than 0.2 wt % based on the weight of the polymer and wherein the molar ratio of peroxy functionalities from said peroxide (p) to metal (M) ranges from 1 to 100; said metal (M) being selected from the group consisting of Sn(II), Sb(III), Pb(II), Bi(III), Fe(II), Ti(II), Ti(III), Mn(II), Mn(III), and Ge(II).

2. The process according to claim 1 wherein the polymer is obtained by polymerizing one or more monomers, dimers, and/or oligomers using a Sn(II), Sb(III), Pb(II), Bi(III), Fe(II), Ti(II), Ti(III), Mn(II), Mn(III), or Ge(II)-containing catalyst.

3. The process according to claim 1 wherein the polymer is obtained by ring-opening melt polymerization.

4. The process according to claim 1 wherein the polymer is a poly(hydroxy acid).

5. The process according to claim 1 wherein said peroxide is selected from the group consisting of organic hydroperoxides, ketone peroxides, and mixtures thereof.

6. The process according to claim 5 wherein the peroxide is an organic hydroperoxide.

7. The process according to claim 6 wherein the hydroperoxide is a hydroperoxide selected from the group consisting of 1,1,3,3-tetramethylbutyl hydroperoxide, cumyl hydroperoxide, t-butyl hydroperoxide, t-amyl hydroperoxide, and 1,2-diisopropylbenzene monohydroperoxide.

8. A process for preparing a poly(hydroxy acid) comprising the steps of: a) converting one or more monomers, dimers, and/or oligomers of a hydroxy acid into a poly(hydroxy acid) using a Sn(II), Sb(III), Pb(II), Bi(III), Fe(II), Ti(II), Ti(III), Mn(II), Mn(III), or Ge(II)-containing catalyst and b) treating the poly(hydroxy acid) at a temperature above its melting temperature with a peroxide selected from the group consisting of ketone peroxides, organic hydroperoxides, peracids, hydrogen peroxide, and mixtures thereof, wherein said peroxide is used in an amount less than 0.2 wt % based on the weight of the poly(hydroxy acid) and wherein the molar ratio of perm functionalities from said peroxide (p) to metal (M) ranges from 1 to 100; M being selected from the group consisting of Sn(II), Sb(III), Pb(II), Bi(III), Fe(II), Ti(II), Ti(III), Mn(II), Mn(III), and Ge(II).

9. The process according to claim 8 wherein step (a) is performed by ring-opening melt-polymerization.

10. The process according to claim 8 wherein the poly (hydroxy acid) is a polylactide.

11. A polylactide obtained by the process according to claim 10.

12. The process according to claim 8 wherein the catalyst is a Sn(II)-containing catalyst and the metal is Sn(II).

13. The process according to claim 12 wherein the Sn(II)-containing catalyst is Sn(II) 2-ethylhexanoate.

14. The process according to claim 8 wherein said peroxide is selected from the group consisting of organic hydroperoxides, ketone peroxides, and mixtures thereof.

15. The process according to claim 14 wherein the peroxide is an organic hydroperoxide.

16. The process according to claim 15 wherein the hydroperoxide is a hydroperoxide selected from the group consisting of 1,1,3,3-tetramethylbutyl hydroperoxide, cumyl hydroperoxide, t-butyl hydroperoxide, t-amyl hydroperoxide, and 1,2-diisopropylbenzene monohydroperoxide.

\* \* \* \* \*